(12) United States Patent
Zhang et al.

(10) Patent No.: US 9,856,227 B2
(45) Date of Patent: Jan. 2, 2018

(54) METHOD FOR THE PRODUCTION OF ETHYLENE OXIDE

(71) Applicant: Dow Technology Investments LLC, Midland, MI (US)

(72) Inventors: Liping Zhang, Lake Jackson, TX (US); Mark H. McAdon, Midland, MI (US); Ernest R. Frank, Freeport, TX (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 15/409,784

(22) Filed: Jan. 19, 2017

(65) Prior Publication Data

US 2017/0158654 A1    Jun. 8, 2017

Related U.S. Application Data

(62) Division of application No. 14/773,784, filed as application No. PCT/US2014/023925 on Mar. 12, 2014, now Pat. No. 9,573,916.

(60) Provisional application No. 61/794,646, filed on Mar. 15, 2013.

(51) Int. Cl.
| | |
|---|---|
| *C07D 301/03* | (2006.01) |
| *C07C 29/00* | (2006.01) |
| *C07D 301/10* | (2006.01) |
| *C07C 41/02* | (2006.01) |
| *C07C 213/02* | (2006.01) |
| *C07C 29/10* | (2006.01) |
| *C07C 29/132* | (2006.01) |
| *C07D 317/38* | (2006.01) |

(52) U.S. Cl.
CPC ............ *C07D 301/10* (2013.01); *C07C 29/00* (2013.01); *C07C 29/106* (2013.01); *C07C 29/132* (2013.01); *C07C 41/02* (2013.01); *C07C 213/02* (2013.01); *C07D 317/38* (2013.01)

(58) Field of Classification Search
CPC ..... C07C 41/02; C07C 213/02; C07C 29/106; C07C 29/132; C07C 31/202; C07C 43/10; C07C 215/08; C07C 29/00; C07D 301/10; C07D 301/03; C07D 317/38
USPC .......................................... 549/536; 568/865
See application file for complete search history.

(56) References Cited

U.S. PATENT DOCUMENTS

| | | |
|---|---|---|
| 3,950,507 A | 4/1976 | Boreskov et al. |
| 4,761,394 A | 8/1988 | Lauritzen |
| 4,994,587 A | 2/1991 | Notermann et al. |
| 5,187,140 A | 2/1993 | Thorsteinson et al. |
| 5,504,053 A | 4/1996 | Chou et al. |
| 6,080,897 A | 6/2000 | Kawabe |
| 6,511,938 B1 | 1/2003 | Liu et al. |
| 6,727,389 B1 | 4/2004 | Viswanathan |

(Continued)

FOREIGN PATENT DOCUMENTS

| | | |
|---|---|---|
| WO | 2012050819 A1 | 4/2012 |
| WO | 2014150669 A1 | 9/2014 |

OTHER PUBLICATIONS

Zhang Declaration submitted to USPTO on Jun. 11, 2009.

(Continued)

*Primary Examiner* — T. Victor Oh
(74) *Attorney, Agent, or Firm* — Hansen IP Law PLLC

(57) ABSTRACT

A method for the production of ethylene oxide wherein the partial pressure of water vapor at the inlet of the reactor is at least about 8 kPa using a high purity carrier comprising alpha-alumina, a promoting amount of at least one Group IA metal, and a promoting amount of rhenium.

9 Claims, 2 Drawing Sheets

(56) References Cited

U.S. PATENT DOCUMENTS

| | | |
|---|---|---|
| 7,193,094 B2 | 3/2007 | Chipman et al. |
| 7,615,655 B2 | 11/2009 | Zhang et al. |
| 8,309,771 B2 | 11/2012 | Noronha et al. |
| 8,362,284 B2 | 1/2013 | Zhang et al. |
| 8,389,751 B2 | 3/2013 | Zhang et al. |
| 8,513,444 B2 | 8/2013 | Habenschuss et al. |
| 8,536,353 B2 | 9/2013 | Matusz |
| 8,546,592 B2 | 10/2013 | Evans et al. |
| 8,845,975 B2 | 9/2014 | Henstock et al. |
| 9,573,916 B2 | 2/2017 | Zhang et al. |
| 2010/0036176 A1 | 2/2010 | Noronha et al. |
| 2010/0056816 A1 | 3/2010 | Wallin et al. |
| 2010/0267974 A1 | 10/2010 | Zhang et al. |

OTHER PUBLICATIONS

Berty, Chemical Engineering Communications, 1989, vol. 82, p. 229-232.
Berty, Applied Industrial Catalysis, 1983, vol. I, at 207-236.
Berty, Studies in Surface Science and Catalysis, 1999, vol. 124, No. 5, pp. 51.
PCT/US2014/023925, International Search Report and Written Opinion dated Jul. 31, 2014.
PCT/US2014/023925, International Preliminary Report on Patentability dated Sep. 24, 2015.

METHOD FOR THE PRODUCTION OF ETHYLENE OXIDE

CROSS-REFERENCE TO RELATED APPLICATIONS

This is a divisional of U.S. patent application Ser. No. 14/773,784, filed on Sep. 9, 2015, which is a national phase entry of Patent Cooperation Treaty Application No. PCT/US2014/23925, filed on Mar. 12, 2014, which claims the benefit of U.S. Provisional Patent Application No. 61/794,646, filed on Mar. 15, 2013. The entirety of each of the foregoing applications is hereby incorporated by reference.

FIELD

The present invention relates to a method for the production of an ethylene oxide, an ethylene glycol, an ethylene glycol ether, an ethylene carbonate or an ethanol amine.

INTRODUCTION

Vapor phase water is introduced into the ethylene oxide reactor in a typical commercial reactor in the feed gas at the inlet of the reactor as well as by generation within the reactor due to the complete combustion of a portion of the ethylene fed to the reactor to carbon dioxide and water.

U.S. Pat. No. 8,546,592 states that it is "well known that low $CO_2$ levels are useful in improving the selectivity of high selectivity catalysts. See, e.g., U.S. Pat. No. 7,237,677; U.S. Pat. No. 7,193,094; US 2007/0129557; WO 2004/07873; WO 2004/07874; and EP 2,155,708. These patents also disclose that water concentrations in the reactor feed should be maintained at a level of at most 0.35 mole percent, preferably less than 0.2 mole percent." Col. 1, lines 53-60. To provide these low levels of water concentration, U.S. Pat. No. 8,546,592 teaches controlling presence of the water vapor in the catalyst bed such that the ratio of the partial pressure of water (PPH2O) divided by the vapor pressure of water (VPH2O) is less than 0.006, preferably less than 0.004. U.S. Pat. No. 8,546,592 describes a number of ways by which the ratio of the partial pressure of water (PPH2O) divided by the vapor pressure of water (VPH2O) can be reduced. One or more of the methods described in U.S. Pat. No. 8,546,592 requires additional capital and/or energy costs for the plant operation (e.g., increasing the cooling of the overhead streams coming from the ethylene oxide removal and/or carbon dioxide removal sections of the plant that return to the ethylene oxide reactor, operation of the reactor at a higher temperature than required) or other undesirable consequences (e.g., reduction in work rate).

It is desirable to provide a method for the production of ethylene oxide without having to expend the capital and/or energy needed to keep, or incur other undesirable consequences of keeping, the inlet water concentration at such low levels.

SUMMARY

We have found a method for the production of ethylene oxide wherein the partial pressure of water vapor at the inlet of the reactor is at least about 8 kPa. The method comprises providing to a reactor a reactor inlet gas mixture comprising ethylene, oxygen, one or more gas phase promoters, water and carbon dioxide, the components of the gas mixture subsequently being contacted within the reactor under epoxidation reaction conditions with a catalyst comprising a catalytically effective amount of silver supported on high purity carrier, a promoting amount of at least one Group IA metal, and a promoting amount of rhenium. A reactor outlet gas mixture comprising ethylene oxide, ethylene, oxygen, water and carbon dioxide is yielded from the reactor. At least a portion of the reactor outlet gas mixture is provided to an ethylene oxide absorber to produce an ethylene oxide stream and a treated gas stream comprising water and carbon dioxide. At least a portion of the treated gas stream is provided to a carbon dioxide absorber unit to partially remove carbon dioxide. The carbon dioxide absorber unit produces a recycle gas stream comprising carbon dioxide and water. At least a portion of the recycle gas stream from the carbon dioxide absorber unit is combined with fresh feeds comprising oxygen and ethylene and at least a portion of a remaining portion, if any, of the treated gas stream to form the reactor inlet gas mixture. The partial pressure of water vapor at the inlet of the reactor is continuously maintained at at least about 8 kPa over a period corresponding to the production of at least 250 kmole of ethylene oxide per cubic meter of catalyst.

In an additional embodiment, the method comprises providing to a reactor a reactor inlet gas mixture comprising ethylene, oxygen, one or more gas phase promoters, water and carbon dioxide, wherein the one or more gas phase promoters are organic chlorides, the components of the gas mixture subsequently being contacted within the reactor under epoxidation reaction conditions with a catalyst comprising a catalytically effective amount of silver supported on high purity carrier, a promoting amount of at least one Group IA metal, and a promoting amount of rhenium. A reactor outlet gas mixture comprising ethylene oxide, ethylene, oxygen, water and carbon dioxide is yielded from the reactor. At least a portion of the reactor outlet gas mixture is provided to an ethylene oxide absorber to produce an ethylene oxide stream and a treated gas stream comprising water and carbon dioxide. At least a portion of the treated gas stream is combined with fresh feeds comprising ethylene and at least a portion of the combined stream is provided to a carbon dioxide absorber unit to partially remove carbon dioxide. At least a portion of the recycle gas stream from the carbon dioxide absorber unit is combined with fresh feeds comprising oxygen and at least a portion of a remaining portion, if any, of the treated gas stream to form the reactor inlet gas mixture. The partial pressure of water vapor at the inlet of the reactor is continuously maintained at at least about 8 kPa over a period corresponding to the production of at least 250 kmole of ethylene oxide per cubic meter of catalyst.

Surprisingly and unexpectedly, in the production of ethylene oxide using such catalysts, the rate of ethylene oxide production per volume of the catalyst is maintained or even increased as compared to the rate of ethylene oxide production per volume of the same catalyst under the same epoxidation reaction conditions except that the partial pressure of water vapor at the reactor inlet is less than about 8 kPa.

DETAILED DESCRIPTION

Figure 1:
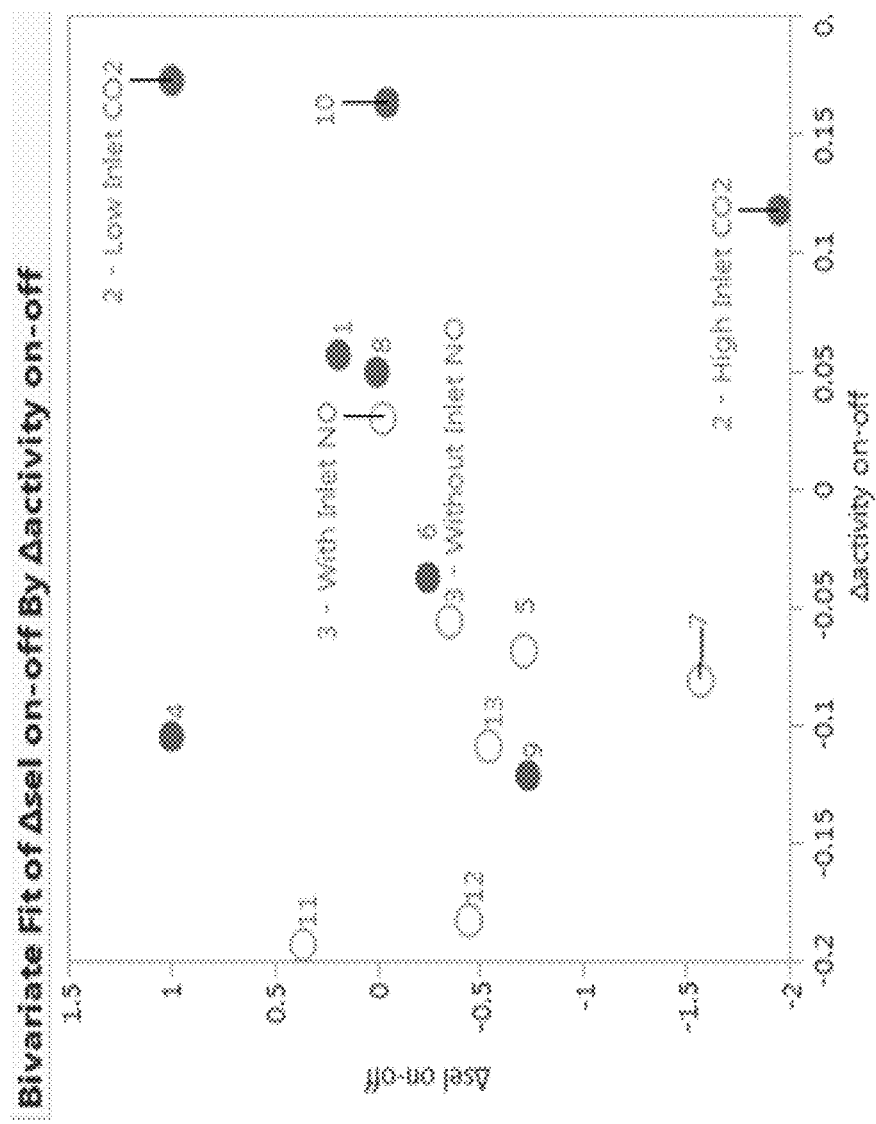
FIG. 1 depicts the bivariate analysis (delta selectivity of added water on-off vs delta activity, measured by change in $\Delta EO$ at constant reactor temperature, of added water on-off) of Catalyst Nos. 1 through 13 of the Examples herein.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof; rather, and unless otherwise noted, terms are to be understood according to conventional usage by those of ordinary skill in the relevant art. Unless defined otherwise, technical and scientific terms used herein have the same meaning as is commonly understood by one of skill in the art to which this invention belongs.

The "efficiency" of the oxidation, which is synonymous with "selectivity," refers to the total amount, in molar percent, of converted or reacted ethylene that forms a particular product. For example, the "selectivity to ethylene oxide" refers to the percentage on a molar basis of converted or reacted olefin that forms ethylene oxide. Certain "high efficiency" or "high selectivity" silver-based catalysts are highly selective towards ethylene oxide production. For example, when using certain modern catalysts in the epoxidation of ethylene, the theoretically maximal efficiency towards ethylene oxide can reach values above 85.7 percent, for example 88 percent, or 89 percent, or above. As used herein, the terms "high efficiency catalyst" and "high selectivity catalyst" refer to a catalyst that is capable of producing ethylene from ethylene and oxygen at an efficiency greater than 85.7 percent. The observed actual efficiency of a high efficiency catalyst may fall below 85.7 percent under certain conditions based on process variables, catalyst age, etc. However, if the catalyst is capable of achieving at least an 85.7 percent efficiency, at any point during its life, for example, under any set of epoxidation reaction conditions, or by extrapolating lower efficiencies observed at two different oxygen conversions obtained by varying gas hourly space velocity to the limiting case of zero oxygen conversion, it is considered to be a high efficiency catalyst.

The "activity" of a catalyst can be quantified in a number of ways, one being the mole percent of ethylene oxide contained in the outlet stream of the reactor relative to that in the inlet stream (the mole percent of ethylene oxide in the inlet stream typically, but not necessarily, approaches zero percent) while the reactor temperature is maintained substantially constant; and another being the temperature required to maintain a given rate of ethylene oxide production. In many instances, activity is measured over a period of time in terms of the mole percent of ethylene oxide produced at a specified constant temperature. Alternatively, activity may be measured as a function of the temperature required to sustain production of a specified constant mole percent of ethylene oxide (concentration). The ethylene oxide concentration relates to the ethylene oxide production rate because the production rate may be obtained by multiplying the delta ethylene oxide concentration as defined hereinbelow and the flow rate of the reactor inlet gas mixture. The ethylene oxide production rate/catalyst volume may be determined by dividing the production rate by the volume of the catalyst bed. Thus, activity may also be measured by the rate of ethylene oxide production/volume of the catalyst bed, for example, the kilograms of ethylene oxide produced per hour per cubic meter of catalyst.

The term "promoter" as used herein refers to a component which works effectively to provide an improvement in one or more of the catalytic properties of the catalyst when compared to a catalyst not containing such component. As used herein, the term "co-promoter" refers to a material that—when combined with a promoter—increases the promoting effect of a reaction for a particular product to a greater extent than would the promoter alone. "Promoters" can be materials that are introduced to catalysts during the preparation of the catalysts (solid phase promoters). In addition, "promoters" can also be gaseous materials that are introduced to the epoxidation reactor feed (gas phase promoters).

A "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), efficiency, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced efficiency at one set of operating conditions may be operated at a different set of conditions wherein the improvement shows up in the activity rather than the efficiency and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

"The partial pressure of the water vapor at the reactor inlet" refers to the partial pressure of water vapor in the reactor inlet gas mixture prior to contacting the catalyst.

The terms "carrier" and "support" are used interchangeably herein. A "high purity" carrier comprises greater than about 95 weight percent alpha-alumina and, as measured by X-ray fluorescence ("XRF"), less than about 0.0637 weight percent sodium the weight percent of the alpha-alumina and the sodium being calculated on the weight of the carrier. The carrier may comprise less than about 0.060, 0.055, 0.054, 0.052, 0.050, 0.045, 0.040, 0.035, 0.030, 0.025, 0.020, 0.015, 0.010, 0.005, 0.004, 0.003, or 0.002 weight percent sodium, calculated on the weight of the carrier.

In a separate embodiment, the high purity carrier comprises greater than about 95 weight percent alpha-alumina and comprises less than 10 mmole/kg of carrier of sodium and potassium combined.

"Surface area," as used herein, refers to the surface area of the carrier as determined by the BET (Brunauer, Emmett and Teller) method by nitrogen as described in the Journal of the American Chemical Society 60 (1938) pp. 309-316.

"Total pore volume" means pore volume of the carrier and is typically determined by mercury porosimetry. The measurements reported herein used the method described in Webb & Orr, Analytical Methods in Fine Particle Technology (1997), p. 155, using mercury intrusion to 60,000 psia using Micromeritics Autopore IV 9520, assuming 130° contact angle, 0.485 N/M surface tension of Hg.

"Porosity" is the proportion of the non-solid volume to the total volume of material. Total pore volume as measured by mercury porosimetry or water absorption may be used to estimate porosity by those of skill in the art. Put another way, porosity is defined as the void volume (unoccupied space) divided by the total volume of the sample.

"Fresh feed" refers to the provision of additional quantities of particular components (e.g., ethylene, oxygen, gas phase promoters, ballast gas) in order to achieve target concentrations in the reactor inlet gas mixture to compensate for losses due to, e.g., conversion to other products, losses through purge streams, absorption into liquid streams, and the like.

The term "Shrink Factor" represents the net volumetric reduction occurring due to the production of the ethylene oxide. For every mole of ethylene oxide produced, there is a net reduction of 0.5 moles of total gas resulting in a corresponding reduction in the volumetric flow rate. The Shrink Factor is typically calculated as follows: $(200+EO_{inlet})/(200+EO_{Outlet})$, where $EO_{inlet}$ and $EO_{outlet}$ are the concentrations of ethylene oxide in the reactor inlet and outlet gas mixtures, respectively. Delta ethylene oxide concentration, also referred to as ΔEO %, is the change in ethylene oxide concentration in mole percent across the reactor and is calculated from the $EO_{inlet}$ and $EO_{outlet}$ as follows: $\Delta EO\% = SF*EO_{outlet} - EO_{inlet}$.

A procedure for preparing a high-purity alpha-alumina carrier involves treatment of a carrier material, particularly gamma-alumina, with an organic or inorganic fluorine-containing substance, preferably in aqueous solution, and thereafter firing the treated carrier at a suitable temperature. The carrier may either be extruded by conventional techniques known to the art and formed into pellets after fluorine treatment and before firing or, alternatively, formed, e.g., extruded, pellets may be fluorine-treated and then fired. The fluorine-containing substance is, preferably, a volatile material or one which can be readily volatilized under firing conditions. Examples of suitable fluorine-containing materials include aluminum trifluoride, ammonium fluoride, hydrofluoric acid, and dichlorodifluoromethane. The fluorine compound is used in an amount sufficient to remove a major portion of the sodium present in the sample. This amount will, of course, vary with the amount of sodium present in the sample but will also depend on other factors, such as the condition under which the carrier is treated, such as the firing temperature and heating rate, as well as the depth of the bed of material being treated, the amount of gamma-alumina being treated, the level of contamination of the gamma-alumina, and how well the firing chamber is sealed. Typically, a suitable amount of fluorine compound is not more than about 4 percent, by weight, based on the weight of the carrier material being treated. Preferably, the fluorine compound is present in a minimum amount of about 0.8 percent, by weight. A suitable firing temperature for fluorine-treated alumina is generally less than about 1,200° C., preferably from a temperature over 750 to about 1,100° C. The rate of heating depends in part on the amount of fluorine compound used. The treatment of support materials with fluorine-containing substances may provide a collateral benefit in converting the support material to one having a "platelet" morphology.

High purity carriers also may be made by the processes described in U.S. Pat. Nos. 3,950,507 and 4,994,587 and WO 2008/054564. High purity carriers can be prepared by optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina. In one embodiment, the carrier material comprises at least about 95 weight percent α-alumina and less than about 30 parts per million acid-leachable alkali metals by weight, the weight percent of the α-alumina and the concentration of the acid-leachable alkali metals being calculated on the weight of the carrier, where the acid-leachable alkali metals are selected from lithium, sodium, potassium, and mixtures thereof. One method of measuring nitric acid leachable alkali metals is to prepare samples in duplicate by leaching 2 grams of unground carrier in about 22 grams 10% nitric acid solution (prepared by adding 10 mL concentrated nitric acid to 90 mL ASTM type 1 water). The samples are heated in a constant temperature oven for one hour at 90° C. The samples are cooled to room temperature and filtered with a 0.45 micron syringe filter. Each solution is then analyzed, such as on a Perkin-Elmer Optima 3300 RL Inductively Coupled Plasma ("ICP") emission spectrometer.

Alternatively, an alpha-alumina support of at least 95% purity can be prepared by compounding (mixing) the raw materials, extrusion, drying and a high temperature calcination. In this case, the starting raw materials usually include one or more alpha-alumina powder(s) with different properties, and a burnout material (usually an organic compound) used in the mix to provide desired porosity after its removal during the calcination step. The levels of impurities in the finished carrier are determined by the purity of the raw materials used, and their degree of volatilization during the calcination step. Common impurities may include silica, alkali and alkaline earth metal oxides and trace amounts of metal and/or non-metal-containing additives.

Further, the high-purity carrier may be prepared by any conventional method of removing sodium metals from a solid, particularly mineral or mineral-type material suitable in other respects as a support material. Such treatment should not, however, affect the mechanical or structural characteristics of the support material to the point where they become impractical, nor chemically alter the support material in a manner which adversely affects the catalytic performance indices of efficiency, activity, or catalyst stability. Typically, the techniques involve extraction and/or volatilization of the sodium present. A suitable extraction procedure may involve conversion of the sodium present to a more easily extractable material either in the same step in which extraction takes place or in separate conversion and extraction steps. A suitable volatilization procedure typically includes an initial step in which the sodium present in the support is converted to a material which is volatile upon heating. In some instances, it may be preferable to initially extract as much of the sodium present as possible, followed by a volatilization procedure to remove residual sodium. Exemplary of extraction or leaching procedures is treatment of the support material with a mineral acid, particularly nitric acid in a concentration of about 10 percent, by volume, at a temperature of about 90° C., for a period of about 1 hour and thereafter washing the carrier with water. The rinsed support material is then dried at a temperature of from about 100 to 1,000° C. for a period of from about 1 to about 3 hours.

The carrier preferably has a surface area, as measured by the B.E.T. method of less than 20 m²/g and more in particular from 0.05 to 20 m²/g. Preferably the B.E.T. surface area of the support is in the range of 0.1 to 10, more preferably from 0.1 to 3.0 m²/g. Preferably, the B.E.T. surface area of the support is at least about 0.5 m²/g, and more preferably, at least about 0.7 m²/g. The alpha-alumina carrier preferably has a total pore volume as measured by mercury porosimetry of from about 0.1 to about 0.85 cc/g by volume, more preferably from about 0.25 cc/g to about 0.75 cc/g and a median pore diameter from about 1 to about 50 microns. The alpha-alumina carrier preferably has a water absorption of from about 10 to about 85%, more preferably from about 25 to about 75%.

The alpha-alumina support can be of any suitable shape. Exemplary shapes of the support includes pills, chunks, tablets, pieces, pellets, rings, spheres, wagon wheels, toroids having star shaped inner and/or outer surfaces, and the like. The support can be of any size suitable for employment in reactors. For example, in a fixed bed ethylene oxide reactor having a plurality of parallel elongated tubes (in a suitable shell) 1 to 3 inches (2.5 to 7.5 cm) outer diameter and 15 to 45 feet (4.5 to 13.5 m) long filled with catalyst, it is desirable to employ alpha alumina support having a rounded shape, such as, for example, spheres, pellets, rings, cross-partitioned rings, penta-rings, tablets, and the like, having diameters from 0.1 inch (0.25 cm) to 0.8 inch (2 cm).

In certain embodiments, the carrier will desirably be comprised largely of particles in the form of platelets having at least one substantially flat major surface having a lamellate or platelet morphology, at least 50 percent of which (by number) have a major dimension of less than about 50 microns. As used herein, the term "platelet" means that a particle has at least one substantially flat major surface, and that some of the particles have two, or sometimes more, flat surfaces. The "substantially flat major surface" referred to herein may be characterized by a radius of curvature of at least about twice the length of the major dimension of the surface.

The method of this invention uses a catalyst which comprises silver as a catalytically active metal. Generally, the high purity carrier is impregnated with a catalytic amount of silver, which is any amount of silver capable of catalyzing the direct oxidation of ethylene with oxygen or an oxygen-containing gas to ethylene oxide. In making such a catalyst, the carrier is typically impregnated (one or more times) with one or more silver compound solutions sufficient to allow the silver to be supported on the carrier.

Catalysts for this method for the production of ethylene oxide may be prepared on the high purity carriers by impregnating the carrier with a solution of one or more silver compounds, depositing the silver throughout the pores of the carrier and reducing the silver compound as is well known in the art. See for example, U.S. Pat. Nos. 6,511,938 and 5,187,140. The reduction of cationic silver to metallic silver may be accomplished during a step in which the catalyst is dried. This may be the case if the impregnation solution comprises a reducing agent, for example, an amine. Impregnation of the carrier is the preferred technique for silver deposition because it utilizes silver more efficiently than coating procedures, the latter being generally unable to effect substantial silver deposition onto the interior surfaces of the carrier.

In addition to silver, the catalyst comprises a promoting amount of at least one Group IA metal and the catalyst further comprises a promoting amount of rhenium. Optional additional solid phase promoters include elements or compounds from the group of nitrogen, sulfur, phosphorus, boron, fluorine, Group IIA metals, molybdenum, tungsten, chromium, titanium, hafnium, zirconium, vanadium, manganese, thallium, thorium, tantalum, niobium, gallium and germanium and mixtures thereof. Preferably the Group IA metals are selected from sodium, lithium, potassium, and cesium. Most preferably the Group IA metal is sodium, lithium, and/or cesium. Examples of some anion promoters that may be employed with the present invention include the halides, for example, fluorides and chlorides, and the oxyanions of the elements other than oxygen having an atomic number of 5 to 83 of Groups 3b to 7b and 3a to 7a of the Periodic Table. Manganese promoters may be provided by, for example, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylenediaminetetraacetic acid (EDTA) or a suitable salt thereof.

Examples of solid phase promoter compositions and their characteristics as well as methods for incorporating the promoters as part of the catalyst are described in U.S. Pat. Nos. 5,187,140, 6,511,938, 5,504,053, 5,102, 848, 4, 916, 243, 4,908,343, and 5,059,481, 4,761,394, 4,766,105, 4,808, 738, 4,820,675, and 4,833,261.

Preferably, the catalyst used in the method of the present invention is a high selectivity catalyst.

The method may also be practiced using catalysts which comprise, instead of a promoting amount of rhenium, a promoter of the type comprising at least one efficiency-enhancing salt of a member of a redox-half reaction pair which is employed in an epoxidation process in the presence of a gaseous nitrogen-containing component capable of forming a gaseous efficiency-enhancing member of a redox-half reaction pair under reaction conditions. Catalysts of this type are described in U.S. Pat. Nos. 8,389,751 and 8,362,284.

When used, the rhenium promoter can be provided in various forms, for example, as the metal, as a covalent compound, as a cation or as an anion. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten. Optionally a rhenium co-promoter is used. The rhenium co-promoter may be selected from one or more of sulfur, chromium, molybdenum, tungsten, phosphorus, boron, and compounds thereof.

Silver is present in an amount greater than about 5 percent, greater than about 10 percent, greater than about 15 percent, greater than about 20 percent, greater than about 25 percent, preferably, greater than about 27 percent, and more preferably, greater than about 30 percent by weight, based on the weight of the catalyst. Typically, the amount of silver supported on the carrier is less than about 70 percent, and more preferably, less than about 50 percent by weight, based on the weight of the catalyst.

The rhenium component is often provided in an amount of at least 1 ppmw, at least 5 ppmw, for example, 10 ppmw to 3000 ppmw, often between 20 ppmw and 2000 ppmw, calculated as the weight of rhenium based on the total weight of the catalyst.

The amount of anion promoter may vary widely, for example, from 0.0005 weight percent to 2 weight percent, preferably from 0.001 weight percent to 0.5 weight percent based on the total weight of the catalyst. The concentration of the alkali metal promoters in the finished catalyst is not narrow and may vary over a wide range. The optimum alkali metal promoter concentration for a particular catalyst will be dependent upon performance characteristics, such as catalyst efficiency, rate of catalyst aging and reaction temperature.

The concentration of alkali metal (based on the weight of cation, for example cesium) in the finished catalyst may vary from 0.0005 to 1.0 wt. %, preferably from 0.005 to 0.5 wt. %. The preferred amount of cation promoter deposited on or present on the surface of the support or catalyst generally lies between 10 ppm and 4000 ppm, preferably 15 ppm and 3000 ppm, and more preferably between 20 ppm and 2500 ppm by weight of cation calculated on the total support material. Amounts between 50 ppm and 2000 ppm are frequently most preferable. When the alkali metal cesium is used in mixture with other cations, the ratio of cesium to any other alkali metal and alkaline earth metal salt(s), if used, to achieve desired performance is not narrow and may vary over a wide range. The ratio of cesium to the other cation promoters may vary from 0.0001:1 to 10,000:1, preferably from 0.001:1 to 1,000:1.

The desired amount of the manganese deposited on the carrier may be decided based upon the silver content of the catalyst, the amounts and types of other promoters present and the chemical and physical properties of the support. In one embodiment, the manganese is present on the catalyst in an amount of at least 20 ppmw, more preferably at least 60 ppmw calculated as the weight of manganese. In some embodiments, the amount of manganese on the catalyst intermediate or the catalyst falls within the range of 70 ppmw to 1000 ppmw, preferably 80 ppmw to 500 ppmw calculated as the weight of manganese.

Well known methods can be employed to analyze for the amounts of silver and solid promoters deposited onto the alumina carrier. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

Commercial ethylene oxide processes vary in actual configuration, but the processes have in common three primary sections: reaction system, oxide recovery, and oxide purification. In the reaction system, a reactor inlet gas mixture which comprises ethylene, an oxygen-containing gas, water, carbon dioxide, and one or more gas phase promoters, wherein the gas phase promoters are is introduced into a reactor and subsequently contacted with a catalyst disposed within the reactor.

The oxygen-containing gas may comprise substantially pure oxygen or air. If pure oxygen is used, ballast gases or diluents such as nitrogen or methane may also be included to maintain the oxygen concentration below the maximum level allowed by flammability considerations. The concentration of oxygen in the reactor inlet gas mixture may vary over a wide range, and in practice, flammability is generally the limiting factor for oxygen concentration. Generally, the oxygen concentration in the reactor inlet gas mixture will be at least about one (1) mole percent and preferably at least about two (2) mole percent. The oxygen concentration will generally be no more than about fifteen (15) mole percent and preferably no more than about ten (10) mole percent. The ballast gas (e.g., nitrogen or methane) is generally from about 50 mole percent to about 80 mole percent of the total composition of the reactor inlet gas mixture.

The concentration of ethylene in the reactor inlet gas mixture may vary over a wide range. However, it is preferably at least about eighteen (18) mole percent and more preferably at least about twenty (20) mole percent. The concentration of ethylene in the reactor inlet gas mixture is preferably no greater than about 50 mole percent, and more preferably is no greater than about 40 mole percent.

The gas phase promoter is generally a compound that enhances the efficiency and/or activity of the process for producing ethylene oxide. Preferred gas phase promoters include organic chlorides. More preferably, the gas phase promoter is at least one selected from the group consisting of methyl chloride, ethyl chloride, ethylene dichloride, vinyl chloride, and mixtures thereof. Ethyl chloride and ethylene dichloride are most preferred as the gas phase promoter feed. Using chlorohydrocarbon gas phase promoters as an example, it is believed that the ability of the promoter to enhance the performance (e.g., efficiency and/or activity) of the process for ethylene oxide depends on the extent to which the gas phase promoter chlorinates the surface of the catalyst in the epoxidation reactor, for example, by depositing particular chlorine species such as atomic chlorine or chloride ions on the catalyst. However, hydrocarbons lacking chlorine atoms are believed to strip chlorides from the catalyst, and therefore, detract from the overall performance enhancement provided by the gas phase promoter. Discussions of this phenomenon may be found in Berty, "Inhibitor Action of Chlorinated Hydrocarbons in the Oxidation of Ethylene to Ethylene Oxide," *Chemical Engineering Communications*, Vol. 82 (1989) at 229-232 and Berty, "Ethylene Oxide Synthesis," *Applied Industrial Catalysis*, Vol. I (1983) at 207-238. Paraffinic compounds, such as ethane or propane, are believed to be especially effective at stripping chlorides from the catalyst. However, olefins, such as ethylene and propylene, are also believed to act to strip chlorides from the catalyst. Some of these hydrocarbons may also be introduced as impurities in the ethylene feed. Typically, the preferred concentration of ethane in the reactor inlet gas mixture, when present, is from 0 to about 2 mole percent. Given the competing effects of the gas phase promoter and the chloride-removing hydrocarbons, it is convenient to define an "overall catalyst chloriding effectiveness value" that represents the net effect of the promoting and non-promoting gas phase species in halogenating (or chloriding) the catalyst. "Overall catalyst chloriding effectiveness value" is defined and explained in U.S. Pat. Nos. 8,389,751 and 8,362,284.

In addition to an organic chloride gas phase promoter, one or more gaseous components capable of generating at least one efficiency-enhancing member of a redox half reaction pair may be employed as a gas phase promoters. Both a nitrogen-containing gas phase promoter and an organic chloride gas phase promoter can be used.

The effectiveness of a particular gaseous nitrogen-containing promoter is determined by its ability to generate the active nitrogen and oxygen-containing members of a redox half reaction pair in the catalyst. See U.S. Pat. No. 8,389, 751. As a result, it is preferred to determine experimentally the effectiveness of the gaseous promoter to be used in the process. See U.S. Pat. No. 8,389,751. With catalysts of the type employed in this invention, as the partial pressure of the water vapor in the reactor inlet gas mixture increases, the overall chloriding effectiveness value and the concentrations of the gaseous nitrogen-containing promoters (if present) should be re-optimized, generally resulting in a decrease in the value of such levels.

In the reaction system, the reactor inlet gas mixture is provided to an oxidation reactor which contains the catalyst. Conventional, commercial fixed-bed ethylene-oxide reactors are suitable for use in the present invention, and they include a plurality of parallel elongated tubes that have inside diameters in the range of from about 20 to 66 mm. The tubes are packed with the catalyst that provides for the partial oxidation of ethylene with oxygen to ethylene oxide. The tubes are typically suitable for use in a shell-and-tube type reactor and are formed into a bundle for placement into the shell of the reactor. The epoxidation reaction is generally exothermic and thus requires a coolant system. Thus, a coolant system (e.g., a cooling jacket or a hydraulic circuit with a coolant fluid such as a heat transfer fluid or boiling water) is provided to regulate the temperature of the epoxidation reaction.

The epoxidation reaction temperature is in the range of from about 200° C. to 300° C. It should be noted that the terms "reaction temperature," "epoxidation temperature" or "epoxidation reaction temperature" refer to any selected temperature(s) that are directly or indirectly indicative of the catalyst bed temperature. Thus, the reaction temperature may be a catalyst bed temperature at a specific location in the catalyst bed, a numerical average of several catalyst bed temperature measurements made along one or more catalyst bed dimensions (e.g., along the length), the reactor outlet gas temperature, the reactor coolant outlet temperature or the reactor coolant inlet temperature.

The epoxidation reaction is carried out at a temperature that is preferably at least about 200° C., more preferably at least about 210° C., and most preferably at least about 220° C. Reaction temperatures of no more than 300° C. are preferred, and reaction temperatures of no more than about 290° C. are more preferred. Reaction temperatures of no more than about 280° C. are most preferred. The reactor pressure is selected based on the desired mass velocity and productivity and ranges generally from about 5 atm (506 kPa) to about 30 atm (3.0 MPa). The gas hourly space velocity (GHSV) is preferably greater than about 3000 $hr^{-1}$, more preferably greater than about 4,000 $hr^{-1}$, and most preferably greater than about 5,000 $hr^{-1}$.

The resulting reactor outlet gas mixture comprises ethylene oxide product, carbon dioxide, water, as well as unreacted ethylene and oxygen, a ballast gas or diluent such as methane or nitrogen. The gas is sent to the ethylene oxide recovery section.

In general, the recovery section in the ethylene oxide process involves the absorption and refining of ethylene oxide. In the ethylene oxide absorber, a water stream is used to separate the ethylene oxide from the other gases, creating an ethylene oxide stream and a treated gas stream. The ethylene oxide stream is removed from the ethylene oxide absorber. Ethylene oxide absorbers are described in US Publication 2010/0036176A1 and U.S. Pat. No. 6,727,389. The treated gas stream or some portion of the treated gas stream, is sent from the ethylene oxide absorber to a carbon dioxide absorber unit. Optionally, a fresh feed comprising ethylene may be combined with at least a portion of the treated gas stream to form a combined stream and at least a portion of this combined stream is sent to the carbon dioxide absorber unit.

A portion of the portion of the treated gas stream or combined stream that is fed to the carbon dioxide absorber unit exits the carbon dioxide absorber unit as a recycle stream, and is mixed with fresh feeds (oxygen and optionally ethylene) and at least a portion of a remaining portion, if any, of the treated gas stream and fed back to the oxidation reactor. The reactor inlet gas mixture comprises ethylene, carbon dioxide which was not removed in the carbon dioxide absorber unit, water, oxygen gas and other gases, such as the gas phase promoters, as well as the ballast gas. A "remaining portion, if any, of the treated gas stream" is the portion, if any, of the treated gas stream that is not sent to the carbon dioxide absorber unit nor purged from the reaction process.

The partial pressure of the water vapor at the reactor inlet is continuously maintained at at least about 8 kPa for the production of at least 250 kmole of ethylene oxide per cubic meter (kmole $m^{-3}$) of the catalyst, at least about 500, 1000, 2000, 2500, 5000, 7500, 10,000, 15,000, 20,000, 25,000, 50,000, 75,000, 100,000, or 200,000 kmole of ethylene oxide per cubic meter (kmole $m^{-3}$) of the catalyst, where the volume of the catalyst is measured as the packed volume of the reactor. Alternatively, for a larger scale production of ethylene oxide (e.g., one where more than about 25 kg of catalyst are charged to a reactor ("catalyst charge"), the partial pressure of the water vapor in the reactor inlet gas stream is continuously maintained at at least about 8 kPa for at least one quarter of the time before the catalyst charge is exchanged, at least one-third of the time before the catalyst charge is exchanged, one-half of the time before the catalyst charge is changed, or at least three-quarters of the time before the catalyst charge is exchanged. The "packed volume of the reactor" is the volume of the reactor that is actually occupied by the catalyst bed.

The partial pressure of the water vapor at the reactor inlet is at least about 8 kPa, 9 kPa, 10 kPa, 11 kPa, 12 kPa, 13 kPa, 14 kPa, 15 kPa, 16 kPa, 17 kPa, 18 kPa, 19 kPa, 20 kPa, 25 kPa, 30 kPa, 33 kPa, 35 kPa or 40 kPa. Preferably, the partial pressure of the water vapor at the reactor inlet is no more than about 60 kPa, 50 kPa or 40 kPa.

Those of skill in the art will appreciate that the partial pressure of water vapor at the reactor inlet can be increased, for example, by the introduction of water or by steam injection or by increasing the temperature of the recycle stream from the carbon dioxide absorber unit and/or the treated stream from the ethylene oxide absorber.

The ethylene oxide produced by the present epoxidation method may typically be processed to provide further downstream products, such as, for example, ethylene glycols, ethylene glycol ethers, ethylene carbonates, and ethanol amines. Since the present invention provides an improved epoxidation method, it is contemplated that the improvements provided will carry forward to provide improvements to these downstream processes and/or products. Improved methods for the production of such glycols, carbonates, ethers and ethanol amines are thus also provided herein.

The conversion of ethylene oxide into ethylene glycols or ethylene glycol ethers may comprise, for example, reacting the ethylene oxide with water, suitably in the presence of an acidic or basic catalyst. For example, for preferential production of the ethylene glycol over the ethylene glycol ether, the ethylene oxide may be reacted with a tenfold molar excess of water, in a liquid phase reaction in the presence of an acid catalyst, e.g., 0.5-1.0 wt % sulfuric acid, based on the total reaction mixture, at from about 50° C. to about 70° C. at 1 bar absolute, or in a gas phase reaction, at from about 130° C. to about 240° C. and from about 20 bar to about 40 bar absolute, preferably in the absence of a catalyst. If the proportion of water is lowered, the proportion of the ethylene glycol ethers in the reaction mixture will be increased. The ethylene glycol ethers thus produced may comprise di-ethers, tri-ethers, tetra-ethers or other multi-ethers. Alternative ethylene glycol ethers may be prepared by converting the ethylene oxide with an alcohol, such as methanol or ethanol, or by replacing at least a portion of the water with the alcohol. The resulting ethylene glycols and ethylene glycol ethers may be utilized in a wide variety of end-use applications in the food, beverage, tobacco, cosmetic, thermoplastic polymer, curable resin system, detergent, heat transfer system, etc., industries.

The conversion of ethylene oxides produced via the method of the present invention into ethanol amines may comprise, for example, reacting the ethylene oxide with ammonia. Anhydrous or aqueous ammonia may be used, although anhydrous ammonia favors the production of mono ethanol amine, and may be used when the same is preferred. The resulting ethanol amines may be used, for example, in the treatment of natural gas. The ethylene oxide may be converted into the corresponding ethylene carbonate by reacting the ethylene oxide with carbon dioxide. If desired, an ethylene glycol may be prepared by subsequently reacting the ethylene carbonate with water or an alcohol to form the ethylene glycol. For applicable methods, reference is made to U.S. Pat. No. 6,080,897.

EXAMPLES

Carrier Properties and Composition diameter of 3/16 inch (dimensions after drying). The extruded pellets are dried at 60° C. in flowing air for 36 to 72 h. The dried extrudates are calcined in a 10 cubic foot Unitherm furnace. Between 1.5 and 2 kg of sample are placed in 10"×10"×4" deep saggers. Up to 10 saggers are loaded in to the furnace. Samples are calcined to 700° C. Air is fed into the furnace at 150 SLPM (standard liters per minute). The furnace program is 1) heat from room temperature to 130° C. in 2 h, hold 130° C. for 3 h, heat from 130° C. to 500° C. in 12 h, heat from 500° C. to 700° C. in 4 h, hold 700° C. for 2.5 h, then cool to 25° C. in 6 h. Due to its thermal mass, the Unitherm requires about 2 days to cool to below 40° C. After calcination the samples are weighed.

A 2 cubic foot graphite reactor is based on a Centorr/Vacuum Industries Series 3700 Model 12"×12"×24" graphite vacuum furnace. The furnace is plumbed to a gas handling system controlled by a control system. The gas handling system allows for the controlled addition of gases and the removal and scrubbing of reactor process gas. The calcined samples are loaded into graphite boxes (10.75"×

TABLE 1

| Carrier ID | A | B | C | D | E | F | G | H** | I** |
|---|---|---|---|---|---|---|---|---|---|
| Surface Area (m²/g) | 1.35 | 0.89 | 0.87 | 1.19 | 0.85 | 1.29 | 0.97 | 0.80 | 0.94 |
| Pore volume (cc/g) | Est. approx. 0.6 to 0.8 | 0.28 | 0.53 | | 0.52 | 0.7 | 0.66 | | 0.62 |
| Water absorption (%) | | 28 | 54.1 | 52.4 | 52.6 | | | 53.3 | |
| Platelet morphology (Y/N) | Y | N | N | N | N | Y | Y | N | Y |
| XRF Analysis* (wt %) | | | | | | | | d | d | d |
| Na | <0.002 | 0.482 | 0.0637 | <0.002 | 0.326 | <0.002 | <0.002 | 0.326 | <0.002 |
| Al | 52.77 | 52.39 | 52.61 | 52.69 | 51.37 | 52.07 | 52.74 | 51.37 | 52.07 |
| Si | 0.0116 | 0.0365 | 0.0702 | 0.0661 | 0.861 | 0.0274 | 0.0272 | 0.861 | 0.0274 |
| P | <0.002 | <0.002 | <0.002 | <0.002 | 0.0034 | <0.002 | <0.002 | 0.0034 | <0.002 |
| S | 0.0021 | <0.002 | <0.002 | <0.002 | <0.002 | <0.002 | 0.0031 | <0.002 | <0.002 |
| Cl | 0.0235 | 0.0209 | 0.0211 | 0.0171 | 0.0267 | 0.0165 | 0.0197 | 0.0267 | 0.0165 |
| K | <0.002 | 0.0432 | 0.0094 | 0.0055 | 0.238 | <0.002 | 0.0045 | 0.238 | <0.002 |
| Ca | 0.0245 | 0.0572 | 0.104 | 0.0847 | 0.134 | 0.0169 | 0.0165 | 0.134 | 0.0169 |
| Ti | 0.0593 | 0.0061 | 0.0083 | 0.0068 | 0.0072 | 0.0897 | 0.0921 | 0.0072 | 0.0897 |
| V | 0.0031 | <0.002 | <0.002 | <0.002 | <0.002 | <0.002 | <0.002 | <0.002 | <0.002 |
| Cr | 0.0024 | 0.0022 | 0.0035 | 0.0044 | 0.0027 | 0.0022 | <0.002 | 0.0027 | 0.0022 |
| Fe | 0.0153 | 0.029 | 0.0398 | 0.0304 | 0.0378 | 0.0066 | 0.0055 | 0.0378 | 0.0066 |
| Ni | 0.003 | <0.002 | <0.002 | <0.002 | <0.002 | <0.002 | <0.002 | <0.002 | <0.002 |
| Zn | <0.002 | <0.002 | <0.002 | <0.002 | <0.002 | <0.002 | 0.0041 | <0.002 | <0.002 |
| Ga | 0.0023 | 0.01 | 0.0127 | 0.0067 | 0.0121 | 0.0025 | 0.0022 | 0.0121 | 0.0025 |
| Sr | <0.002 | <0.002 | 0.0024 | <0.002 | <0.002 | <0.002 | <0.002 | <0.002 | <0.002 |
| Zr | <0.002 | <0.002 | 0.0021 | 0.0066 | 0.0023 | 0.942 | <0.002 | 0.0023 | 0.942 |
| Mo | <0.002 | <0.002 | <0.002 | <0.002 | <0.002 | 0.0029 | <0.002 | <0.002 | 0.0029 |
| Hf | <0.002 | <0.002 | <0.002 | <0.002 | <0.002 | 0.0057 | <0.002 | <0.002 | 0.0057 |

"d" indicates that the XRF analysis is for the same type of carrier identified in Table 1, although not from the exact carrier.
*The compositional analysis of the supports are performed by a semi-quantitative X-Ray Fluorescence (XRF) method. The analysis is performed on whole support pills positioned in a sample cup, covered, and held in place with a 6 micron polypropylene film. The sampling area is purged with helium during acquisition, and the SuperQ Uniquant program analysis method on the Axios$^{mAX}$-Advance XRF instrument is used.
**Carrier H is a blend of two batches of carrier prepared by the same manufacturing process. The surface area and water absorption values reported above are the weighted average surface area and water absorption for the blend. Carrier I is a blend of two batches of carrier prepared by the same manufacturing process. The surface area and total pore volume values reported above are the weighted average surface area and total pore volume for the blend.

Carrier Preparation

Carrier A. Carrier pellets are prepared by paste extrusion. 1:1 Catapal B/Versal V-250 samples are made by adding 50 parts by weight of UOP Versal V-250, 50 parts by weight of Sasol Catapal B to a stainless steel mix-muller along with 6.5 parts by weight Methocel™ A4M and 3 parts by weight oleic acid. After mulling "dry" for 5 min, 64 parts by weight of water are added and then mulled "wet" for 15 min. The resulting paste mixture is extruded with a counter-rotating twin screw extruder at 120 rpm through a die to form 5/16 inch diameter hollow pellets of equal length, with an inner 10.75"×1.75") and then loaded into the graphite reactor. The reactor is evacuated, and heated to the initial reaction temperature 820° C., the evening before the reaction. The reactor and samples are held under a dynamic vacuum at the initial reaction temperature until the reaction is initiated the next morning. To initiate the reaction, HFC-134a is added to the reactor to a pressure of approximately 100 torr. After incubation for 3 hours at 820° C., the reactor is heated at 2° C./min to the final reaction temperature 930° C. The final reaction temperature is held for 2 hours before the reactor is cooled at about 5° C./min. When the temperature reaches 930° C., the automatic purge/fill cycles are initiated. The automatic purge/fill cycle consists of evacuation to 50 torr followed by filling with $N_2$ to 600 torr. A total of 6 cycles are performed. The reactor is allowed to cool. Nitrogen is evacuated from the reactor, the cooled reactor is filled with air, opened, and the carrier removed. The carrier is then heat treated. Heat treatment of the carrier is performed in an electric furnace in air. The heating profile consists of a 5° C. heating ramp to 800° C. This temperature is maintained for 2 h, after which time the samples are allowed to cool to room temperature at approximately 10° C. $h^{-1}$.

Carrier B is a carrier available from Saint Gobain Norpro (Ohio USA) under the product code SA5502.

Carrier C is a carrier available from Saint Gobain Norpro under the product code SA5562.

Carrier D is a carrier available from Saint Gobain Norpro under the product code SA55333.

Carriers E and H are conventional alpha-alumina supports having the properties set forth in Table 1 above.

Carriers F and I are provided by Saint-Gobain Norpro and prepared by mixing zirconium silicate with boehmite alumina (AlOOH) and gamma-alumina, peptizing the aluminas with a mixture containing an acidic component and fluoride anions, forming (for example, by extruding or pressing) the mixture into pellets, drying the pellets, and calcining the dried pellets.

Carrier G is provided by St Gobain Norpro and uses boehmite alumina (AlOOH) and gamma-alumina, peptizing the aluminas with a mixture containing an acidic component and fluoride anions, forming (for example, by extruding or pressing) the mixture into pellets, drying the pellets, and calcining the dried pellets.

mixing 1.14 parts of ethylenediamine (high purity grade) with 1.75 parts of distilled water; (2) slowly adding 1.16 parts of oxalic acid dihydrate (reagent grade) to the aqueous ethylenediamine solution such that the temperature of the solution does not exceed 40° C., (3) slowly adding 1.98 parts of silver oxide, and (4) adding 0.40 parts of monoethanolamine (Fe and Cl free).

The alpha-alumina carrier is impregnated under vacuum with the silver impregnation solution. The carrier remains immersed in the silver impregnation solution at ambient conditions for 5 to 30 minutes. The impregnated carrier is then taken out and thereafter drained of excess solution for 10 to 30 minutes.

The impregnated carrier is then roasted to effect reduction of silver on the carrier surface. For roasting, the impregnated carrier is spread out in a single layer on a stainless steel belt of spiral weave and transported through a heating zone for 2.5 minutes. The heating zone is maintained at 500° C. by passing hot air upward through the belt and the impregnated carrier. After roasting in the heating zone, the impregnated carrier is kept in the open and brought to room temperature and weighed.

The impregnated carrier is vacuum impregnated with a second silver impregnation solution. The second impregnation solution includes one or more of the following promoters, depending upon the catalyst formulation: manganese, rhenium, sodium, cesium, lithium, sulfate, and potassium. Following the second impregnation, the impregnated carrier is drained of excess solution and roasted as described previously.

The properties of the catalysts are shown in Table 2.

TABLE 2

| Cat No. | 1 | 2 | 3 | 4 | 5 | 6 | 7 |
|---|---|---|---|---|---|---|---|
| Carrier | A | A | A | B | B | C | C |
| Promoters (ppm) | K: 2039 Mn: 251 | Re: 875 Mn: 102 Cs: 794 Na: 65 Li: 50 $SO_4$: 127 | Mn: 72 Cs: 355 Na: 32 Li: 27 $SO_4$: 201 | Re: 446 Mn: 88 Cs: 384 Na: 36 Li: 29 $SO_4$: 55 | Mn: 77 Cs: 387 Na: 37 Li: 29 $SO_4$: 219 | Re: 369 Mn: 45 Cs: 678 Na: 48 Li: 47 $SO_4$: 210 | Mn: 80 Cs: 400 Na: 38 Li: 31 $SO_4$: 224 |
| Silver (wt % of catalyst) | 35.8 | 35.2 | 36.3 | 16.7 | 18.1 | 29.35 | 28.7 |

| Cat No. | 8 | 9 | 10 | 11 | 12 | 13 |
|---|---|---|---|---|---|---|
| Carrier | D | E | F | G | H | I |
| Promoters (ppm) | Re: 378 Mn: 43 Cs: 567 Li: 48 $SO_4$: 210 | Re: 378 Mn: 43 Cs: 567 Li: 48 $SO_4$: 210 | Re: 978 Mn: 115 Cs: 835 Na: 57 Li: 47 $SO_4$: 113 | K: 3 Mn: 94 Cs: 552 Li: 19 $SO_4$: 150 | Cs: 571 Na: 3691 $SO_4$: 860 | Mn: 71 Cs: 339 Na: 31 Li: 24 SO4: 187 |
| Silver (wt) % of catalyst) | 28.45 | 28.45 | 35.0 | 32.7 | 28.0 | 32.1 |

Carriers A, D, F, G and I are high purity carriers as defined in this application.

Catalyst Preparation

The carriers are vacuum impregnated with a first impregnation silver solution typically containing up to 30 weight percent silver oxide, 18 weight percent oxalic acid, 17 weight percent ethylenediamine, 6 weight percent monoethanolamine, and 27 weight percent distilled water. The first impregnation solution is typically prepared by (1)

For Catalysts 1-10, the catalyst composition is determined by mass balance. For Catalysts 11 and 12, the catalyst composition is determined by XRF. For Catalyst 13, sodium, lithium and sulfate are determined by mass balance and manganese and cesium are determined by XRF.

Catalyst Testing Protocol

Figure 2:
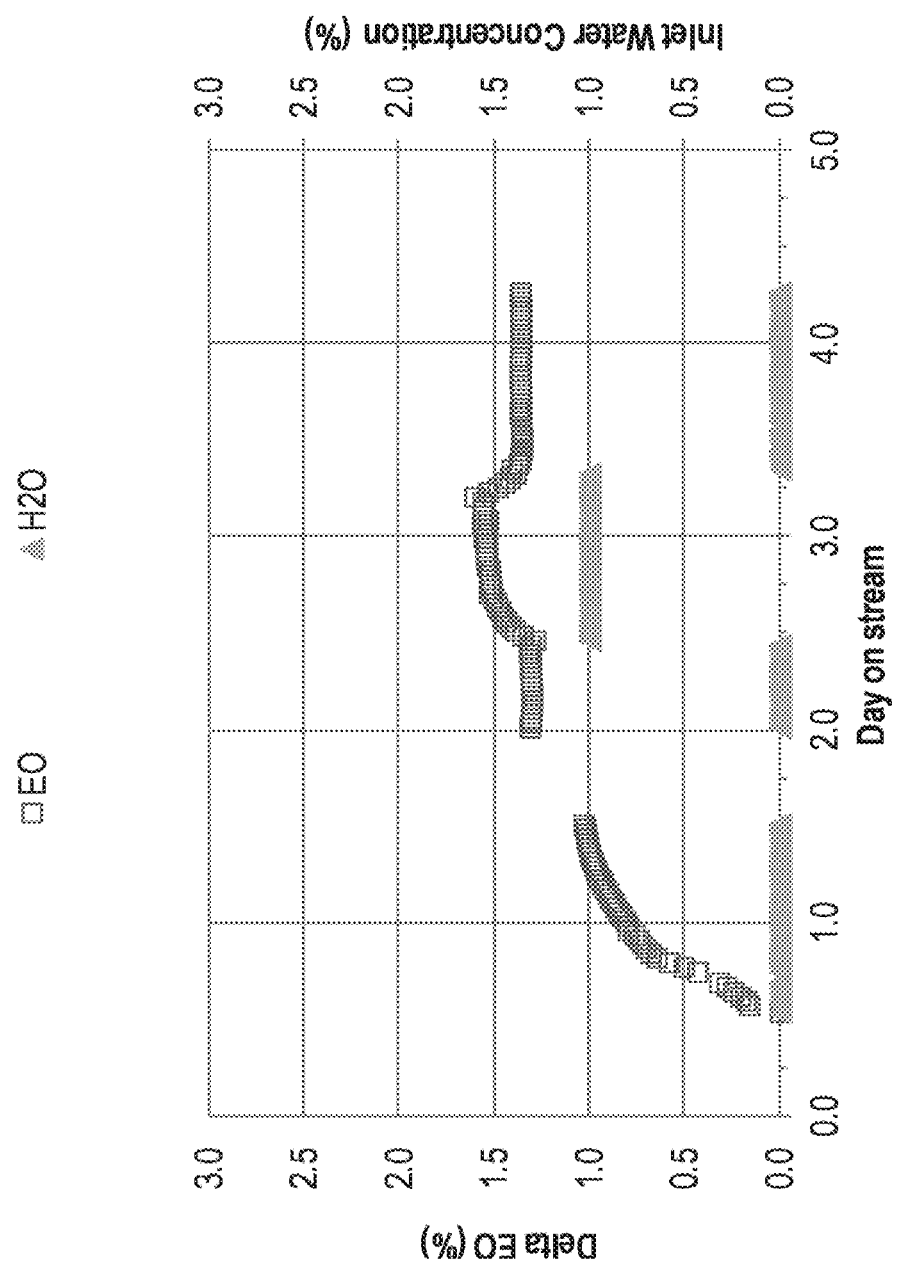
FIG. 2 depicts a plot of the observed effects of the test according to the Catalyst Testing Protocol, of Catalyst 2, under Condition 1.

A standard back-mixed continuous stirred tank reactor (CSTR) is used for catalyst testing. Well known, CSTR, bottom-agitated reactors as shown in FIG. 2.4.4 of the work by J. M. Berry entitled "Experiments in Catalytic Reaction Engineering"," in Studies in Surface Science and Catalysis, Vol. 124, No. 5, pages 51, 1999, may be used.

For the examples below, each catalyst is tested under one of the sets of Conditions 1, 2, or 3 below. The Conditions listed below are the inlet conditions and the reactor is operated at a constant temperature such that catalyst activity is measured by the delta ethylene oxide concentration.

| Ethylene Epoxidation Inlet Process Conditions | | | |
|---|---|---|---|
| Component | 1 Mole % | 2 Mole % | 3 Mole % |
| Ethylene | 30.0 | 30.0 | 30.0 |
| Oxygen | 8.0 | 8.0 | 8.0 |
| Ethane | 0.75% | 0.75 | 0 |
| Carbon Dioxide | 0 | 5.0 | 0% |
| Nitrogen | Balance of gas | Balance of gas | Balance of gas |
| Ethyl Chloride | As provided in Table 3 | As provided in Table 3 | As provided in Table 3 |
| NO | | | 7 ppmv |
| Total Inlet Flow Rate | 11.3 SCFH | 11.3 SCFH | 11.3 SCFFI$^c$ |

The pressure is maintained at about 275 psig (pounds per square inch, gauge) (2000 kPa absolute) and the total flow is maintained at about 11.3 SCFH (Standard Cubic Feet per Hour). SCFH refers to cubic feet per hour at standard temperature and pressure, namely, 0° C. and one atmosphere. LPH refers to liters per hour at standard temperature and pressure. The flow rate is calibrated with a nitrogen stream. A constant reactor temperature as given in Table 3 is maintained and catalyst activity is measured by the delta ethylene oxide concentration produced in the reactor. When water is added to the reactor inlet, it is fed as a liquid from a Gilson Model 307 pump through a ¹⁄₁₆" stainless steel tubing fitting attached directly to the inlet gas inlet tubing of the reactor. The water is vaporized inside of the reactor prior to contacting the catalyst. A sample of the gas at the inlet is taken prior to feeding the water. The inlet water concentration is set by the volumetric flow rate from the pump and independently verified by the analyzed water concentration on the reactor outlet. When feeding water, the inlet gas composition and inlet flow rate are adjusted or not as indicated in Table 3 to account for the added volumetric flow of the water so that the inlet gas composition and reactor conditions are maintained in the presence of the added inlet water.

The catalyst test procedure involves the following: approximately 40 cm³ of catalyst is charged to the back-mixed CSTR and the weight of the catalyst is noted. The back-mixed CSTR is heated to reaction temperature in a nitrogen flow of 2-10 SCFH with the fan operating at 1500 rpm. Once the reactor has achieved the desired temperature, the nitrogen flow is replaced by the above-described feed stream. The total gas inlet flow is then adjusted to 11.3 SCFH for 40 cm³ of catalyst.

Data collected comparing catalyst performance in the presence and absence of water in the feed is obtained from a CSTR operating at the conditions described. The analysis of the reactor inlet and outlet gas composition is obtained from a Thermo Scientific Prima dB process mass spectrometer. The analysis method utilized may or may not specifically analyze the water content in the gas streams; it is desirable if water is analyzed because this can provide a method of independently verifying that the water introduction system is operating nominally. The water introduction system to the reactor, as noted, introduces water after the reactor inlet gas composition is analyzed. Therefore, the presence of water in the feed can be determined by comparing the measured outlet water composition to the carbon dioxide concentration produced by the reaction; a higher measured water concentration in the reactor outlet than measured concentration of carbon dioxide produced by the reaction is an independent verification that the water feed system is functioning properly and also provides a validation of the inlet water concentration. The concentration of water in the reactor inlet and outlet gas concentration must be accounted for in the reported normalized gas concentrations from the process mass spectrometer for proper calculation of delta concentrations, balances, and catalyst efficiencies.

For the data analysis, the data points, corresponding to approximately 11 hours of stable reactor operation, are selected. For conditions where water is being fed, the last 20 data points collected while water is being fed are selected to correspond to the "water on" condition. Once water feed is terminated, a period of time is allowed for the reactor performance to stabilize and 20 additional data points corresponding to the "water off" condition are selected for analysis. (Catalyst 5 had only 12 data points due to an unplanned laboratory shut-down.) The data is then analyzed for statistical outliers and these are eliminated from further analysis. The average measured ΔEO concentrations (%) and carbon efficiencies (%) for each of these "water on" and "water off" conditions are then calculated and analyzed.

Results of this analysis are shown in Table 3. Also shown is the calculated standard error of the mean calculated from the data sets analyzed; this provides an indication of the error of the measured mean.

TABLE 3

| Catalyst No. | 1 | 2 | 2 | 3 | 3 | 4 | 5 |
|---|---|---|---|---|---|---|---|
| Ethylene Epoxidation Inlet Process Condition | 3 | 1 | 2 | 2 | 3 | 1 | 2 |
| Parameter Measured | | | | | | | |
| ΔActivity Water on- Water off (% ΔEO) | 0.057 | 0.17 | 0.12 | −0.056 | 0.030 | −0.10 | −0.069 |
| Δ Carbon Efficiency Water on- Water off | 0.19 | 1.00 | −1.94 | −0.34 | −0.026 | 1.00 | −0.70 |
| Δ Activity - Standard Error | 0.0011 | 0.0094 | 0.0063 | 0.0049 | 0.018 | 0.0026 | 0.0094 |
| Δ Efficiency - Standard Error | 0.012 | 0.044 | 0.071 | 0.027 | 0.12 | 0.044 | 0.061 |
| Activity (% DEO) "Water On" | 1.86 | 1.54 | 1.84 | 2.14 | 2.38 | 1.51 | 1.14 |
| % Carbon Selectivity "Water On" | 85.91 | 87.33 | 79.77 | 77.64 | 76.86 | 80.27 | 73.95 |
| % ΔEO Standard Error of the Mean - Water On | 0.00096 | 0.0094 | 0.0035 | 0.0048 | 0.017 | 0.0018 | 0.0084 |
| % Carbon Efficiency Standard Error of the Mean - Water on | 0.0099 | 0.042 | 0.042 | 0.024 | 0.11 | 0.035 | 0.042 |

TABLE 3-continued

| | | | | | | | |
|---|---|---|---|---|---|---|---|
| Activity (% DEO) "Water off" | 1.81 | 1.36 | 1.72 | 2.20 | 2.35 | 1.62 | 1.21 |
| % Carbon efficiency "Water off" | 85.72 | 86.33 | 81.71 | 77.98 | 76.89 | 79.27 | 74.65 |
| % ΔEO Standard Error of the Mean - Water Off | 0.00059 | 0.00045 | 0.0052 | 0.00088 | 0.0048 | 0.0018 | 0.0042 |
| % Carbon Efficiency Standard Error of the Mean - Water Off | 0.0074 | 0.011 | 0.057 | 0.0 | 0.034 | 0.027 | 0.044 |
| Catalyst Weight (g) | 34.3 | 32.0 | 30.1 | 32.0 | 32.0 | 43.4 | 41.2 |
| Reaction Temperature (° C.) | 240 | 230 | 235 | 235 | 240 | 237 | 245 |
| Compensation for water (Y/N) | Y | Y | Y | Y | Y | Y | Y |
| Ethyl chloride (ppmv) | 5 | 2.2 | 5 | 5 | 5 | 1.8 | 5 |

| Catalyst No. | 6 | 7 | 8 | 9 |
|---|---|---|---|---|
| Ethylene Epoxidation Inlet Process Condition | 1 | 2 | 1 | 1 |
| Parameter Measured | | | | |
| ΔActivity Water on- Water off (% ΔEO) | −0.037 | −0.081 | 0.050 | −0.12 |
| Δ Carbon Efficiency Water on- Water off | −0.24 | −1.56 | 0.0059 | −0.72 |
| Δ Activity - Standard Error | 0.0015 | 0.0061 | 0.0028 | 0.0090 |
| Δ Efficiency - Standard Error | 0.024 | 0.074 | 0.037 | 0.049 |
| Activity (% DEO) "Water On" | 1.33 | 1.70 | 1.93 | 1.27 |
| % Carbon Selectivity "Water On" | 82.52 | 77.35 | 81.31 | 77.86 |
| % ΔEO Standard Error of the Mean - Water On | 0.14 | 0.0052 | 0.0025 | 0.0067 |
| % Carbon Efficiency Standard Error of the Mean - Water on | 0.04 | 0.030 | 0.035 | 0.044 |
| Activity (% DEO) "Water off" | 1.33 | 1.78 | 1.88 | 1.39 |
| % Carbon efficiency "Water off" | 82.76 | 78.91 | 81.31 | 78.58 |
| % ΔEO Standard Error of the Mean - Water Off | 0.00060 | 0.0032 | 0.0013 | 0.0060 |
| % Carbon Efficiency Standard Error of the Mean - Water Off | 0.19 | 0.067 | 0.012 | 0.023 |
| Catalyst Weight (g) | 37.3 | 37.3 | 29.9 | 23.7 |
| Reaction Temperature (° C.) | 237 | 235 | 245 | 245 |
| Compensation for water (Y/N) | Y | Y | N | N |
| Ethyl chloride (ppm) | 1.8 | 5 | 3.1 | 4.2 |

| Catalyst No. | 10 | 11 | 12 | 13 |
|---|---|---|---|---|
| Ethylene Epoxidation Inlet Process Condition | 1 | 2 | 2 | 2 |
| Parameter Measured | | | | |
| ΔActivity Water on- Water off (% ΔEO) | 0.16 | −0.19 | −0.18 | −0.11 |
| Δ Carbon Efficiency Water on- Water off | −0.044 | 0.36 | −0.44 | −0.53 |
| Δ Activity - Standard Error | 0.0012 | 0.0056 | 0.0015 | 0.0015 |
| Δ Efficiency - Standard Error | 0.012 | 0.065 | 0.022 | 0.027 |
| Activity (% DEO) "Water On" | 1.74 | 1.99 | 1.62 | 1.90 |
| % Carbon Selectivity "Water On" | 87.66 | 79.35 | 76.95 | 79.07 |
| % ΔEO Standard Error of the Mean - Water On | 0.00093 | 0.0052 | 0.00093 | 0.0013 |
| % Carbon Efficiency Standard Error of the Mean - Water on | 0.0091 | 0.058 | 0.019 | 0.025 |
| Activity (% DEO) "Water off" | 1.58 | 2.18 | 1.81 | 2.01 |
| % Carbon efficiency "Water off" | 87.70 | 78.98 | 77.39 | 79.60 |
| % ΔEO Standard Error of the Mean - Water Off | 0.00069 | 0.0021 | 0.0011 | 0.00085 |
| % Carbon Efficiency Standard Error of the Mean - Water Off | 0.0073 | 0.029 | 0.010 | 0.011 |
| Catalyst Weight (g) | 32.4 | 33.2 | 32.4 | 32.9 |
| Reaction Temperature (° C.) | 240 | 235 | 245 | 235 |
| Compensation for water (Y/N) | N | N | N | N |
| Ethyl chloride (ppm) | 3.7 | 3.5 | 5.5 | 5 |

Hypothetical Example

Approximately 4.4 kg of an ethylene oxide catalyst are charged to each tube of a multi-tubular ethylene oxide reactor having reactor tubes with inside diameter of 1.28 inches and a depth of 18.8 feet. The catalyst comprises a catalytically effective amount of silver supported on a high purity carrier, and a promoting amount of cesium, sodium, lithium, sulfate, manganese and rhenium. The inlet gas pressure is 1550 kPa absolute. A gas mixture is passed through the catalyst bed. The gas hourly space velocity is 5000 $hr^{-1}$. The composition of the gas mixture comprises 30 mole percent ethylene, 8 mole percent oxygen, 0.5 mole percent carbon dioxide, water, ethyl chloride at a concentration adjusted to maintain optimal selectivity and methane as ballast gas. The initial water vapor partial pressure at the inlet of the reactor is below 8 kPa. The components of this gas mixture are subsequently contacted within the reactor with the catalyst.

The reaction temperature is initially targeted at 225° C. and then adjusted so as to achieve a desired rate of ethylene oxide production per volume of catalyst. The efficiency for ethylene oxide production exceeds 85.7%.

The reactor yields a reactor outlet gas mixture comprising ethylene oxide, ethylene, oxygen, water and carbon dioxide. The reactor outlet gas mixture is provided to an ethylene oxide absorber to produce an ethylene oxide stream and a treated gas stream comprising water and carbon dioxide. A portion of the treated gas stream is provided to a carbon dioxide absorber unit. The carbon dioxide absorber unit is operated to produce a recycle gas stream comprising carbon dioxide and water. Substantially all of the recycle gas stream from the carbon dioxide absorber unit is combined with fresh feeds comprising oxygen, ethylene, as well as the majority of the remaining portion of the treated gas stream to form the reactor inlet gas mixture.

After the production 2500 kmole of ethylene oxide per cubic meter of catalyst, the partial pressure of the water vapor at the reactor inlet is increased to above 8 kPa, and the inlet ethyl chloride concentration is re-optimized. The reaction temperature is decreased to maintain the desired rate of ethylene oxide production per volume of catalyst and the efficiency is observed to increase. The partial pressure of the water vapor at the reactor inlet is continuously maintained at above 8 kPa for the further production of at least 250 kmole of ethylene oxide per cubic meter of catalyst.

Example

A catalyst comprising a catalytically effective amount of silver supported on a high purity carrier and promoting amounts of at least one group IA metal and rhenium is operated in a plug flow reactor, achieving a total production of approximately 55000 kmoles of EO per cubic meter of catalyst. After achieving this production, the catalyst is discharged in eight sequential sections. Approximately 42.5 cc of the fifth section (toward the reactor outlet) is charged into a CSTR (back-mixed) reactor and heated to 200° C. under a nitrogen flow. Upon reaching that target temperature, water is added at the reactor inlet to this nitrogen flow for one hour, with a target water concentration of 1.2% in the total reactor inlet gas, whereupon the nitrogen gas to the reactor is replaced with an inlet gas feed mixture having a target composition (as measured by mass spectrometric analysis of the inlet gas mixture upstream of the water addition point) of 30.4% ethylene, 0.4% ethane, 8.1% oxygen, 3.2 ppm ethyl chloride, a balance of nitrogen, a pressure of 275 psig (2000 kPa absolute), and a total flow of 10.7 SCFH (standard cubic feet per hour). The reactor temperature is then increased to 255° C. As the reactor temperature is being increased, the flow rates of the feed gases are fine tuned so that the calculated inlet feed concentrations downstream of the water addition point are 30% ethylene, 8% oxygen, 0.4% ethane, and 1.2% water (a partial pressure of 24 kPa water), with the inlet ethyl chloride concentration being adjusted over the next few days to maximize catalyst selectivity to ethylene oxide at this temperature. The catalyst average performance during 12 hour operation at this ethyl chloride concentration measures 1.8% Delta EO and selectivity of 85.0%. Water to the feed is then shut off, the total flow rate of the feed gas mixture is increased to 10.8 SCFH so that the overall inlet flow rate remains the same in the absence of added water, and the other feeds are adjusted so that their inlet concentrations remain the same in the absence of added water. The inlet ethyl chloride concentration is then varied to again maximize the selectivity. Under these conditions, the average catalyst performance during 12 hours operation is 1.6% Delta EO and selectivity of 84.4%.

What is claimed is:

1. A method of producing ethylene oxide comprising:
   a) providing to a reactor a reactor inlet gas mixture comprising ethylene, oxygen, one or more gas phase promoters, water and carbon dioxide, wherein the one or more gas phase promoters are organic chlorides, the components of the gas mixture subsequently being contacted within the reactor under epoxidation reaction conditions with a catalyst comprising a catalytically effective amount of silver supported on a high purity carrier, a promoting amount of at least one Group IA metal, and a promoting amount of rhenium;
   b) yielding from the reactor a reactor outlet gas mixture comprising ethylene oxide, ethylene, oxygen, water and carbon dioxide;
   c) providing at least a portion of the reactor outlet gas mixture to an ethylene oxide absorber to produce an ethylene oxide stream and a treated gas stream comprising water and carbon dioxide;
   d) providing at least a portion of the treated gas stream to a carbon dioxide absorber unit;
   e) operating the carbon dioxide absorber unit to produce a recycle gas stream comprising carbon dioxide and water; and
   f) combining at least a portion of the recycle gas stream from the carbon dioxide absorber unit with fresh feeds comprising oxygen and ethylene and at least a portion of a remaining portion, if any, of the treated gas stream, to form the reactor inlet gas mixture, wherein:
      (i) a partial pressure of water vapor at the reactor inlet is at least 13 kPa; and
      (ii) the partial pressure of water vapor at the reactor inlet is continuously maintained at a value of at least 13 kPa over a period corresponding to the production of at least 250 kmole of ethylene oxide per cubic meter of catalyst.

2. The method of claim 1, wherein the at least one Group IA metal comprises cesium and/or lithium.

3. The method of claim 1, wherein the at least one Group IA metal comprises cesium and lithium.

4. The method of claim 1, wherein the rate of ethylene oxide production per volume of catalyst is maintained or increased as compared to the rate of ethylene oxide production per volume of catalyst of the same catalyst under the same epoxidation reaction conditions except that the partial pressure of water vapor at the reactor inlet is less than 13 kPa.

5. The method of claim 4, wherein the rate of ethylene oxide production per volume of catalyst is increased as compared to the rate of ethylene oxide production per volume of the same catalyst under the same epoxidation reaction conditions except that the partial pressure of water vapor at the reactor inlet is less than 13 kPa.

6. The method of claim 4, wherein the selectivity of the reaction to ethylene oxide is maintained or increased as compared to the selectivity of the same catalyst under the same epoxidation reaction conditions except that the partial pressure of water vapor at the reactor inlet is less than 13 kPa.

7. The method of claim 6, wherein the selectivity of the reaction to ethylene oxide is increased as compared to the selectivity of the same catalyst under the same epoxidation reaction conditions except that the partial pressure of water vapor at the reactor inlet is less than 13 kPa.

8. The method of claim 1, wherein the partial pressure of water vapor at the reactor inlet is no more than 60 kPa.

9. The method of claim 1, wherein the catalyst is a high selectivity catalyst.

* * * * *